(12) United States Patent
Sacherer

(10) Patent No.: US 8,414,829 B2
(45) Date of Patent: Apr. 9, 2013

(54) DIAGNOSTIC TAPE CASSETTE

(75) Inventor: Klaus-Dieter Sacherer, Kirchheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1082 days.

(21) Appl. No.: 12/390,539

(22) Filed: Feb. 23, 2009

(65) Prior Publication Data

US 2009/0200413 A1 Aug. 13, 2009

Related U.S. Application Data

(63) Continuation of application No. PCT/EP2007/058649, filed on Aug. 21, 2007.

(30) Foreign Application Priority Data

Aug. 22, 2006 (EP) .................................. 06017404

(51) Int. Cl.
*G01N 33/00* (2006.01)
(52) U.S. Cl. ......................................................... 422/66
(58) Field of Classification Search .................. 422/66
See application file for complete search history.

(56) References Cited

U.S. PATENT DOCUMENTS

| 2,602,729 | A | | 7/1952 | Curry |
| 3,602,448 | A | * | 8/1971 | Muensterer .................... 242/547 |
| 3,728,081 | A | * | 4/1973 | Bidanset ......................... 422/66 |
| 4,115,067 | A | | 9/1978 | Lyshkow |
| 4,954,319 | A | * | 9/1990 | Koizumi et al. ................. 422/67 |
| 5,171,397 | A | | 12/1992 | Arnold |
| 2002/0079345 | A1 | | 6/2002 | Shah |
| 2002/0188224 | A1 | | 12/2002 | Roe et al. |
| 2006/0240403 | A1 | | 10/2006 | List et al. |

FOREIGN PATENT DOCUMENTS

DE 4033590 A1 4/1992
DE 102005013685 A1 9/2006

* cited by examiner

*Primary Examiner* — Lore Jarrett
(74) *Attorney, Agent, or Firm* — Krieg DeVault LLP

(57) ABSTRACT

The invention concerns a diagnostic tape cassette comprising an analytical test tape, a supply spool for winding off unused test tape and a take-up spool for winding used test tape, a housing and a rotational lock for the take-up spool at least against inadvertent unwinding of test tape, wherein the rotational lock comprises one of a locking teeth arrangement, friction elements, and a catch spring and spring latch arrangement.

22 Claims, 5 Drawing Sheets

DIAGNOSTIC TAPE CASSETTE

CLAIM OF PRIORITY

The present application is a continuation based on and claiming priority to PCT Application No. PCT/EP2007/058649, filed Aug. 21, 2007, which claims the priority benefit of European Patent Application No. 06 017 404.2, filed Aug. 22, 2006, each of which are hereby incorporated by reference in their entireties.

TECHNICAL FIELD OF THE INVENTION

The present application relates to a diagnostic tape cassette configured for blood glucose testing, comprising an analytical test tape, a supply spool for winding off unused test tape and a take-up spool for winding used test tape, a housing for the spools and a rotational lock for the take-up spool to guard against inadvertent unwinding of test tape.

BACKGROUND

Previously individual test strips have been used in practice for the self-diagnosis of diabetics which are photometrically analyzed after applying a small amount of sample in order to determine the glucose content in the sample (blood or tissue fluid) as accurately and reliably as possible. In order to improve the user-friendliness it has already been suggested that a plurality of tests be provided on a test tape in the form of a tape cassette. It should be possible to insert such tape cassettes as a disposable part into compact hand-held devices in order to enable all required analytical steps to be carried out automatically and rapidly.

Designs for a reversing lock to prevent tape unwinding is generally known, in order to prevent unintentional winding out of used tape contaminated with blood. One exemplary design is disclosed in U.S. Publication No. 2006/0240403. Generally, a lock is provided that allows test tape to be wound forward whereas it should be secured against turning back in the opposite direction of rotation. In this connection it should be noted that diagnostic tape cassettes as consumable parts are mass-produced articles which it should be possible to manufacture as simply as possible and should operate reliably with a high degree of user friendliness.

On this basis the object of the invention is to further improve the test tape systems proposed in the prior art and to achieve particular advantages for their use while being simpler to manufacture.

SUMMARY

This object and others that will be appreciated by a person of ordinary skill in the art have been achieved according to the embodiments of the present invention disclosed herein. In one embodiment, the present invention comprises a diagnostic tape cassette for use with a blood glucose testing device, comprising an analytical test tape, a supply spool and a take-up spool wherein unused portions of the analytical test tape are provided on the supply spool and unwound for use and wherein used portions of the analytical test tape are wound up onto the take-up spool, a housing for the spools, and a rotational lock for the take-up spool configured to prevent inadvertent unwinding of test tape from at least the take-up spool, wherein the rotational lock comprises one of three designs: (i) locking teeth disposed on opposing surfaces of the housing and the take-up spool, the teeth being shifted by an axial movement of the take-up spool between a mutually engaged position and a release position, (ii) a friction element attached to a housing surface which is brought into frictional engagement with a facing contact surface of the take-up spool when the take-up spool is moved axially out of a release position, and (iii) a locking spring attached to the housing and axially pretensioned against the take-up spool which, by means of at least one spring latch, meshes with free-wheel teeth arranged on the front of the take-up spool to prevent against unwinding of a tape loop.

A first concept of the invention is based on the idea of implementing an automatically switching mechanism instead of a lock controlled by the direction of rotation. Accordingly it is proposed that in one embodiment the rotational lock has locking teeth disposed on opposing faces of both the housing and the take-up spool, said teeth being shifted by an axial movement of the take-up spool in its spool axis between a mutually engaged position and a release position. In this manner it is possible to apply or override a locking action as the situation demands. In the engaged position used test tape is reliably prevented from becoming freely accessible by manipulation of the user. In the release position distracting noises are completely avoided and no additional drive torque is required which is also advantageous with regard to energy supply when it is used in hand-held devices. Furthermore, the proposed solution works independently of the coil diameter of the wound test tape and the rotational lock can be manufactured using a few components without complicated free-wheel mechanisms. At the same time the overall size can be kept small so that the functional parts are not important for determining the cassette size.

The locking teeth in one embodiment are in the engaged position when the tape cassette is handled independently of the testing device and are in the release position when the tape cassette is inserted into the testing device, such as by inserting a drive spindle of the device into the take-up spool.

The axial movement of the locking teeth also enables the take-up spool to be freely rotated in both directions of rotation in the release position and locks the take-up spool in both directions of rotation in the engaged position.

In one embodiment for the construction of the tape cassette, the take-up spool comprises a collar and a cylindrical spool body around which the used portions of the test tape can be wound, the collar comprising a disk having a plurality of teeth as the locking teeth.

In order to achieve an automatic shift function, in one aspect the take-up spool is braced against the housing in the direction of the spool axis by means of a return spring. In this connection, the return spring is typically formed on a wall of the housing as a leaf spring or spiral spring and when an annular space is kept free for the test tape between the wall and the locking teeth.

The housing in other aspects has a toothed ring flange as locking teeth.

In order to avoid an unintentional locking action during axial tilting due to high tape tension, in other embodiments the locking teeth of the housing are formed on a ring segment facing away from a last deflecting point for the test tape to be wound on and when the remaining ring segment has no teeth.

An improved form fit in the locking direction can be achieved by means of the fact that the teeth of the locking teeth have asymmetric tooth flanks where the tooth flanks which strike one another in the engaged position when backing the take-up spool, are steeper.

For an easy manufacture, in yet other embodiments the take-up spool is inserted into a chamber of the housing that is free of a physical axis of rotation. The assembly can also be simplified if the take-up spool can be placed on the locking teeth of the housing in any rotational position.

In order to compensate for tolerances, such as in the case of a separately mounted rotary drive, in yet other embodiments the take-up spool is float-mounted in the housing with transverse play with regard to its spool axis. In this case it should be ensured that the transverse play is greater than about 0.2 mm, typically between about 0.3 and about 0.6 mm. In one aspect, the take-up spool has an annular extension which engages in an opening in the housing with transverse play at least in the engaged position of the locking teeth.

According to a second inventive concept the rotational lock comprises a friction element attached to a housing surface which is brought into frictional engagement with a facing contact surface of the take-up spool when the take-up spool is moved axially out of a release position. As a result a locking function can be achieved in a constructionally simple manner in any position of rotation and independently of the direction of rotation.

The friction element in one embodiment can be formed by a friction ring arranged coaxially with respect to the take-up spool, can comprise an elastomer material, such as TPE, and can be formed on the housing surface by injection-molding.

Another improvement is achieved in embodiments in which the housing surface is formed by a ring flange defining an opening and in which the friction element is arranged circumferentially on the ring flange, such as in the area of the rim of the opening. Correspondingly, the contact surface can then be formed by a collar of a cylindrical spool body around which the test tape can be wound. The frictional force is therefore independent of the current diameter of the tape spool on the spool body.

In order to automatically ensure a frictional engagement when the cassette is not in use, in one embodiment the take-up spool is braced against the housing in the direction of the spool axis by means of a return spring such that the frictional engagement occurs under the restoring force of the return spring.

Another inventive concept is that the rotational lock has a locking spring attached to the housing and axially pretensioned against the take-up spool, which permanently meshes with free-wheel teeth arranged on the front of the take-up spool to prevent unwinding of a tape loop. This not only increases protection against manipulation but can also always prevent an unintentional unwinding of a tape loop for example due to jolting and thus maintain a defined tape positioning at a sensor site.

The locking spring in one embodiment is formed on a wall of the housing, such as in a concentric ring structure or spiral spring where an inner member of the locking spring projecting from the wall carries the at least one latch.

In order to minimize the possible angle of backward movement with a given number of teeth, in one aspect the spring latch is designed as a multiple latch to subdivide the locked positions of the free-wheel teeth such that the individual latches are brought into a locking engagement which is displaced over the tooth pitch of the free-wheel teeth.

According to other aspects of this concept, the free-wheel teeth are formed on an end wall of a spool body of the take-up spool which faces the catch spring, and the spool body is supported on the housing by means of an annular collar and possibly also by locking teeth.

In order to achieve a locking action which is dependent on the direction of rotation, in other aspects the free-wheel teeth are formed by a crown gear with an asymmetric tooth profile where the flatter tooth flanks form a slide slope for the spring latch during rotation in the winding direction and the steeper tooth flanks support the spring latch in a form-fitting manner during rotation in the unwinding direction.

In order to minimize friction, in yet other aspects the teeth of the free-wheel teeth have a tooth height which decreases over their width thus shortening the engagement length of the spring latch.

The invention also concerns a test system comprising a test device and a diagnostic tape cassette inserted therein for blood glucose testing where the tape cassette has an analytical test tape, a supply spool for winding off unused test tape and a take-up spool for winding used test tape, a housing for the spools and a rotational lock for the take-up spool at least against inadvertent unwinding of test tape.

In one embodiment of such a system, a drive spindle of the test device engages in the take-up spool when the tape cassette is inserted and thereby lifts out the locking teeth or abolishes the frictional connection of the friction element into the release position.

Another improvement can be achieved in that the drive spindle can be adjusted by a spring in the direction of a drive axis and engages in the take-up spool under spring displacement. In this connection, the drive spindle in a driver bore of the take-up spool transfers a rotary movement by means of at least one driver.

The invention is to be explained in more detail by the following figures and examples.

BRIEF DESCRIPTION OF THE DRAWINGS

The following detailed description of the embodiments of the present invention can be best understood when read in conjunction with the following drawings, where like structure is indicated with like reference numerals and in which.

In order that the present invention may be more readily understood, reference is made to the following detailed descriptions and examples, which are intended to illustrate the present invention, but not limit the scope thereof.

DETAILED DESCRIPTION OF EMBODIMENTS OF THE PRESENT INVENTION

The following descriptions of the embodiments are merely exemplary in nature and are in no way intended to limit the present invention or its application or uses.

Figure 1:
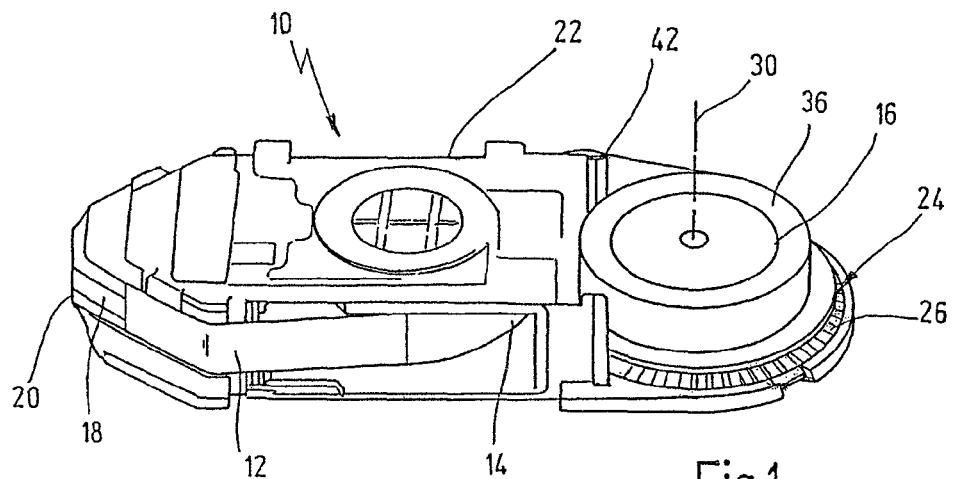
FIG. 1 shows a tape cassette for blood glucose testing comprising an unwinding lock for the test tape in a perspective view.

The tape cassette shown in FIG. 1 with the cover removed enables a plurality of glucose analyses to be carried out locally on blood samples collected by the patients themselves. For this purpose the tape cassette 10 comprises an analytical test tape 12 which can be pulled from a supply spool 14 and wound onto a take-up spool 16, during which a test field 18 is deflected at an application tip 20 in order to allow body fluid (e.g., blood or tissue fluid) to be applied to the front side and a reflectometric measurement to be carried out on the rear side. The test fields 18 mounted on sections of the test tape 12 contain dry chemicals which respond to the analyte (glucose) in the applied body fluid and lead to a measurable change in the light radiated back when the rear side is illuminated.

The spools 14, 16 carrying the test tape 12 are inserted into a housing 22 of the cassette 10 in which housing only the application tip 20 is freely accessible when the cover is fitted. In order to prevent used test tape contaminated with blood from being unintentionally wound off during manipulations from outside, a rotational lock 24 is provided between the take-up spool 16 and housing 22. In the embodiment shown in FIG. 1, this lock is formed by locking teeth 26, 28 formed on respective surfaces of the housing 22 and the take-up spool 16. The take-up spool 16 can be shifted by an axial movement of the take-up spool along the spool axis 30 between a mutually engaged position and a release position.

Figure 2:
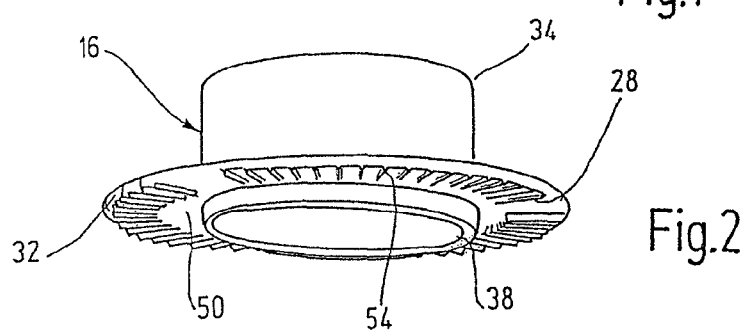
FIG. 2 shows a take-up spool of the tape cassette of FIG. 1 with locking teeth in an enlarged perspective view.

In the embodiment shown in FIG. 2, the take-up spool 16 has a toothed disk 32 with teeth on the front side which carries the locking teeth 28 in the fashion of a crown wheel. The toothed disk 32 is formed by a collar of a hollow-cylindrical spool body 34 around which the test tape 12 can be wound where the locking teeth 28 face away from the spool of test tape 36 (FIG. 1). The take-up spool 16 has an annular extension 38 on the toothed side for a floating centring in the counter-toothing 26.

Figure 3:
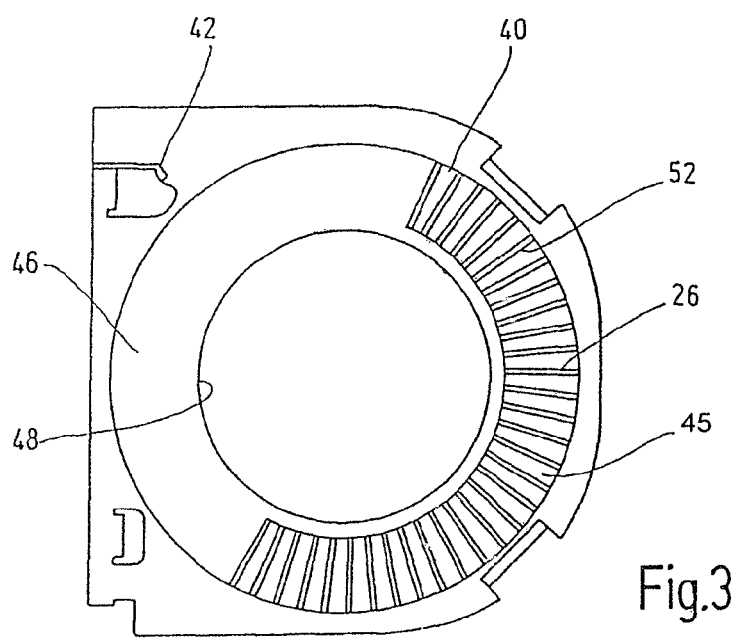
FIG. 3 shows a ring flange of the tape cassette with a counter-toothing in a top-view.

As shown in FIG. 3, the housing 22 has a ring flange 40 which carries the locking teeth 26 on the housing side. Said teeth are formed on a ring segment 45 which faces away from the deflecting point 42 for the test tape 12 to be wound on which is last with regard to the tape transport direction whereas the remaining ring segment 46 has no teeth so that when it is tilted due to a strong tape tensile load of the take-up spool 16, unintentional locking is avoided. The ring flange 40 defines a housing opening 48 in which the annular extension 38 of the take-up spool 16 is pivoted in an engaged position with transverse play 49. This transverse play 49 is achieved by means of the fact that the circumference of the housing opening 48 has an approximately 0.5 mm larger diameter than the annular extension 38. Due to their radial extension the locking teeth 26, 28 can compensate for a corresponding lateral deflection of the take-up spool 16 which can thus compensate for positioning tolerances.

The locking teeth 26, 28 are thus formed in a ring shape on facing surfaces 44, 50 so that the take-up spool 16 can be placed in any rotational position on the ring flange 40. In order to improve the locking action against a reversal of rotation, the teeth of the locking teeth 26, 28 have asymmetric tooth flanks where the tooth flanks 52, 54 that strike each other in the engaged position when the take-up spool 16 is rotated backwards are steeper than the opposing tooth flanks 52, 54.

Figure 4:
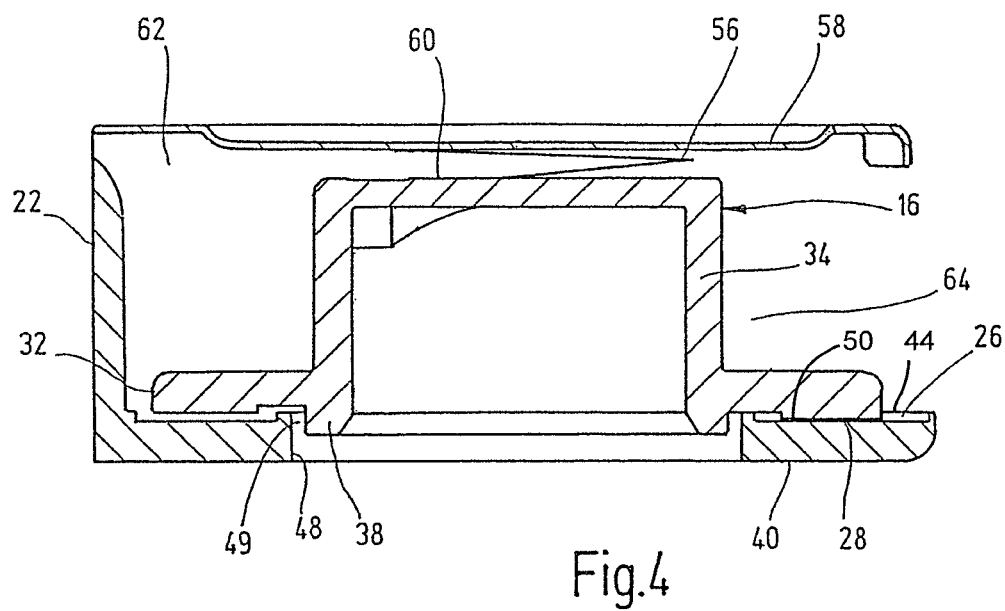
FIGS. 4 and 5 show the take-up spool of the tape cassette and the ring flange of the housing in an engaged position (FIG. 4) and a released position (FIG. 5) of the locking teeth in an axial section.
Figure 5:
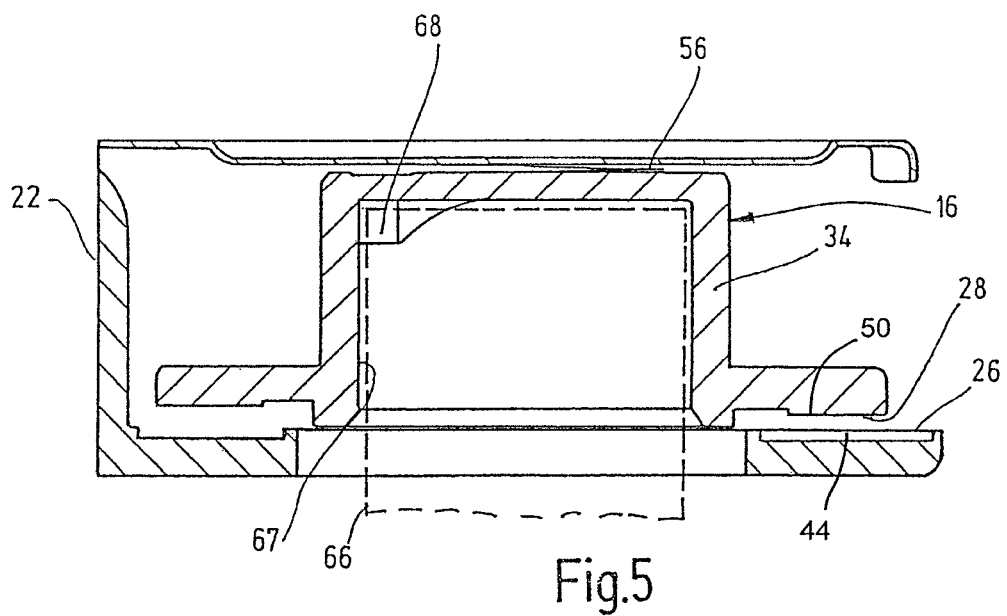

The shifting function of the rotational lock 24 is shown best in FIGS. 4 and 5. When the tape cassette 10 is stored or is handled independently of the device, the locking teeth 26, 28 are mutually engaged so that both directions of rotation are locked by form fitting (FIG. 4). This is ensured by a return spring 56 which is clamped between the cover 58 of the housing 22 and the closed front face 60 of the spool body 34 and presses this against the ring flange 40. The return spring 56 is expediently formed on the cover 58 as a spiral spring. The take-up spool 16 can then be inserted into the housing chamber 62 where no physical pivot axle is required and the annular space 64 between the cover 58 and the rotational lock 24 is kept free in order to receive the test tape 12.

When the tape cassette 10 is used, in one embodiment a drive spindle 66 of an instrument drive which is only shown schematically in FIG. 5 engages axially in the central driver bore 67 of the spool body 34 and thus under compression of the spring 56, results in it being lifted out into the release position. In this process the locking teeth 26, 28 are disengaged and the take-up spool 16 can thus be freely rotated. The drive spindle 66 then optionally adopts the locking function in the unwinding direction whereas the winding on of the test tape—in the example shown when rotated in a clockwise direction—is made possible by three drivers 68 divided in the direction of rotation. Due to the gap between the locking teeth 26, 28 distracting noises are avoided and no undesired braking torque occurs.

Figure 6:
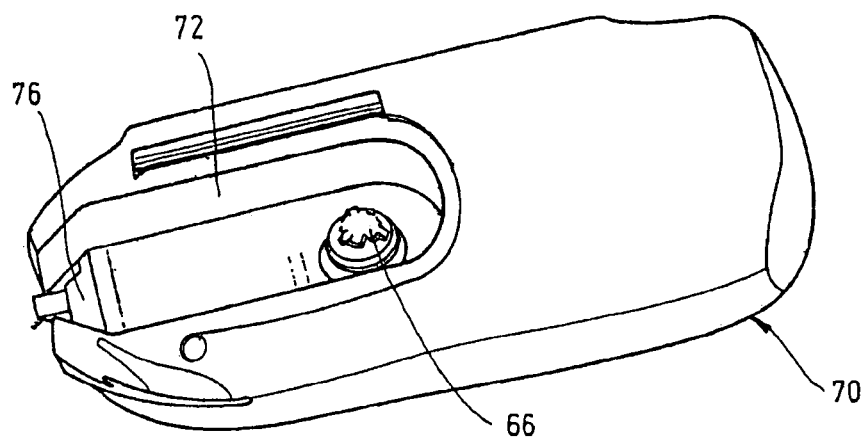
FIG. 6 shows a portable measuring device with a receptacle for the tape cassette in a perspective view.

FIG. 6 shows a hand-held device 70 with a receptacle 72 into which the tape cassette 10 can be inserted in order to enable a substantially automated measuring process with the measuring system that is formed in this manner. The optical measuring system of the instrument 76 is positioned relative to the application tip 20 in the receptacle 72. In this connection the transverse play of the take-up spool 16 explained above allows a compensation of assembly and positioning tolerances of the drive spindle 66 specially mounted in the device housing.

Figure 7:
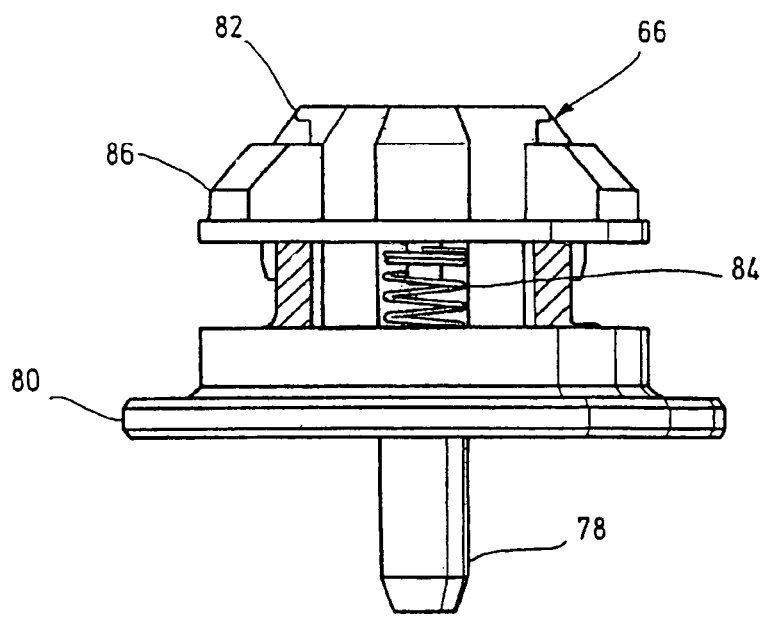
FIG. 7 shows a drive spindle of the device according to FIG. 6 in a side view.

An embodiment of the drive spindle 66 shown separately in FIG. 7 has a driving pin 78 which penetrates the bottom of the receptacle 72 and is coupled via a gearing to a drive motor in the device 70 (not shown). A supporting disk 80 is seated on the pin 78 on which disk a coupling head 82 is supported by means of a helical compression spring 84 allowing axial movement relative to the pin 78. When the cassette 10 is inserted into the receptacle 72, the coupling head 82 plunges into the driver bore 67 of the take-up spool 16 and its circumferential cams 86 come into a form-fit with the drivers 68 under the force of the spring 84 so that a torque can be transferred.

In the embodiments of a rotational lock 24 described in the following description, reference numerals common to other embodiment denote the same or similar structure. The example according to FIGS. 8 to 10 differs essentially in that a locking spring 56' is provided on the housing cover 58 in combination with free-wheel teeth on the take-up spool 16 to permanently secure it against unintentional tape unwinding. As a result the unwinding of a tape loop is avoided in any state of use.

Figure 8:
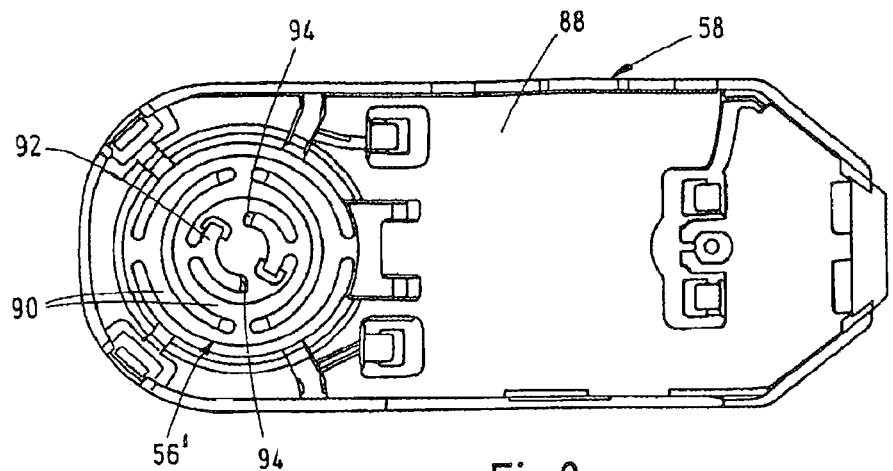
FIG. 8 shows the housing cover with a locking spring that is formed thereon in a further embodiment of the tape cassette.

In the embodiment shown in FIG. 8, the locking spring 56' is punched out of the housing sheet 88 as a ring structure in which two coaxial rings 90 are connected together by bridges. Two ring segments 92 are formed on the inner ring and each has an end bent in each case towards the inside of the housing to form a latch 94 whereas the other piece of the segment is held in a plastic injection-molded encapsulation covering the rear side of the spring 56'. The ring segments 92 and the rings 90 are axially displaced relative to one another such that they form an outwardly curved compression spring arrangement against the front face 60 of the inserted take-up spool 16 (cf. FIG. 10).

Figure 9:
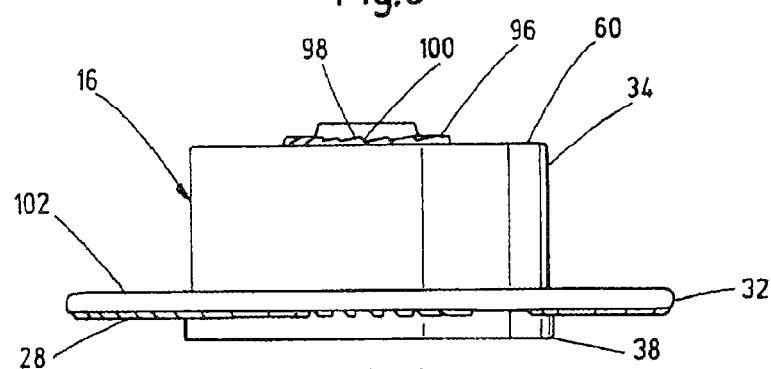
FIG. 9 shows a take-up spool provided with free wheel teeth on the front side in a side view.

FIG. 9 shows an appropriately adapted take-up spool 16 which in contrast to the design of FIG. 2, is provided on its front side with free-wheel teeth 96. This is formed by a crown gear with an asymmetric tooth profile where the flatter tooth flanks 98 form a slide slope for the spring latch 94 when it is rotated in the winding direction and the steeper tooth flanks 100 lock the spring latch 94 in a form-fitting manner when rotated in the unwinding direction.

Figure 10:
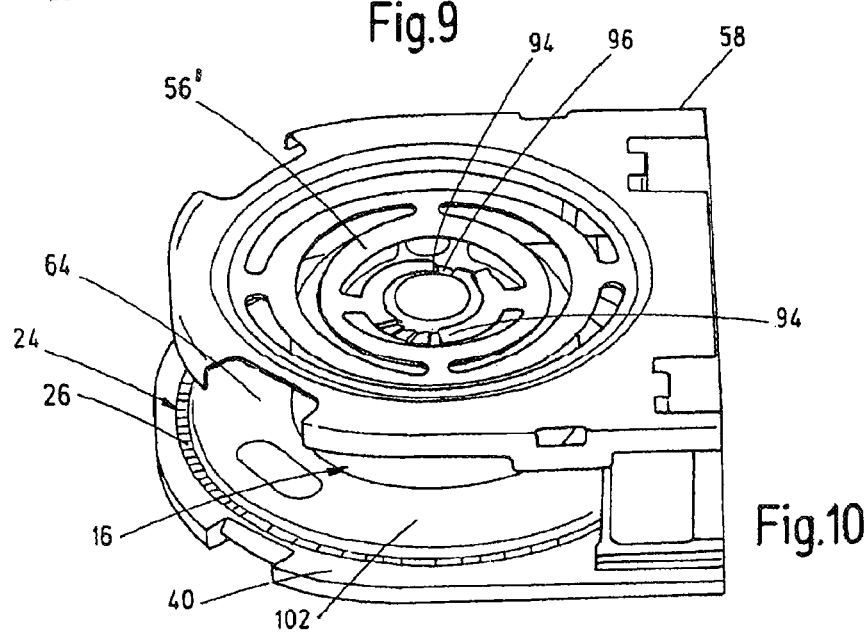
FIG. 10 shows the locking spring according to FIG. 8 engaged with the free wheel teeth according to FIG. 9 for a permanent loop lock in a broken perspective view.

FIG. 10 illustrates the action of the spring engagement which is dependent on the direction of rotation. When the take-up spool 16 is inserted, the latches 94 that are bent downwards mesh under spring pretension such that in the position shown one latch butts against a steep tooth flank 100 whereas the other latch rests centrally on a flat tooth flank 98. In this manner the effective tooth pitch is halved such that a low angle of backward movement is nevertheless achieved until the locking action occurs with a continued and stable interlocking. In order to reduce friction, the teeth of the annular free wheel teeth 96 can have a tooth height which decreases over their width which shortens the engagement length of the spring latches 94.

In order to obtain an additional locking action in both directions of rotation when it is not in use, the collar 102 of the spool body 34 can be provided on its supporting side with circumferential locking teeth 28 which engage in counter-teeth 26 on the housing flange 40. This rotational lock 24 is released by the drive spindle 66 during insertion into the device 70 whereas the directionally-dependent locking action of the rotational lock 94, 96 is retained under higher spring pretension but at a lower engagement angle of the spring latches.

Figure 11:
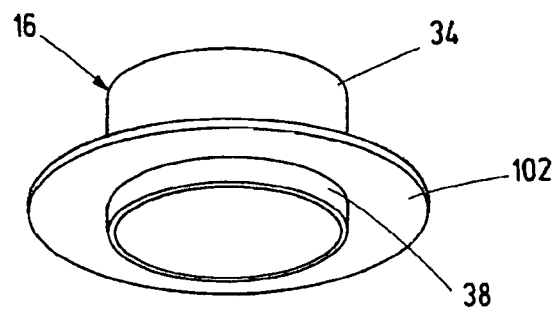
FIGS. 11 to 13 show a further embodiment of the tape cassette with a take-up spool according to FIG. 11 for a frictional engagement with a frictional ring on the housing according to FIG. 12 or 13 in a perspective view.
Figure 12:
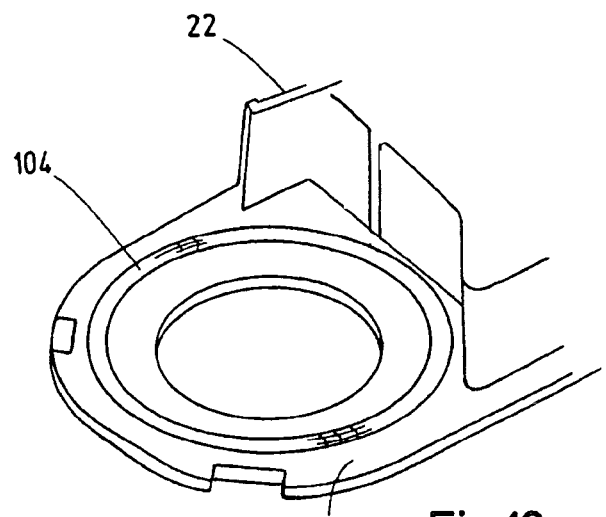
Figure 13:
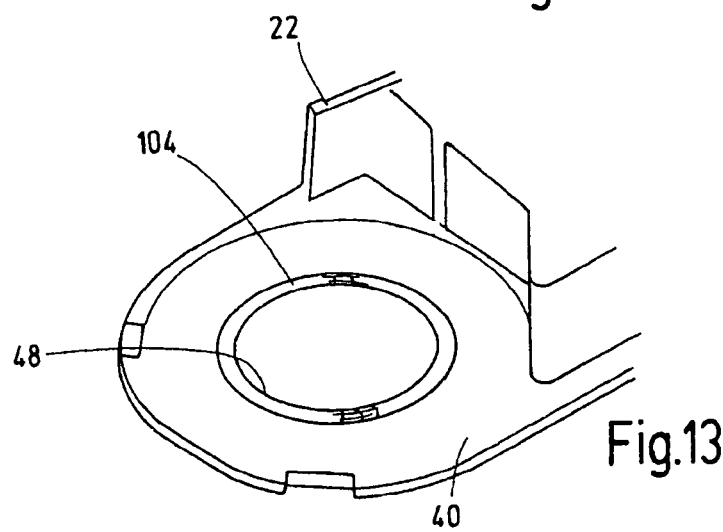

In the embodiment of a rotational lock 24 shown in FIGS. 11 to 13, a friction lock that is independent of the position of rotation and direction of rotation is provided instead of the locking teeth 26, 28. According to FIG. 11, only the collar 102 of the take-up spool 16 remains in this case free of gear teeth. A frictional ring 104 is formed on the support surface of the ring flange 40 of the housing 22 for the frictional lock which either sits in the middle of the ring area (FIG. 12) or at the side of the edge defining the flange opening 48 (FIG. 13). The frictional ring 104 consists of a thermoplastic elastomer material (TPE) which is injection-molded in the same manufacturing step together with sealing components on the housing 22 in an injection-molding process. Also in this case the frictional lock is supported by a return spring 56 according to FIG. 4 formed on the housing 22 whereas when the drive spindle 66 engages according to FIG. 5 the take-up spool 16 is lifted against the force of the spring and thus the frictional connection is released.

The features disclosed in the above description, the claims and the drawings may be important both individually and in any combination with one another for implementing the invention in its various embodiments.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined in the appended claims. More specifically, although some aspects of the present invention are identified herein as preferred or particularly advantageous, it is contemplated that the present invention is not necessarily limited to these preferred aspects of the present invention.

What is claimed is:

1. A diagnostic tape cassette for use with a blood glucose testing device, comprising: an analytical test tape, a supply spool and a take-up spool wherein unused portions of the analytical test tape are provided on the supply spool and unwound for use and wherein used portions of the analytical test tape are wound up onto the take-up spool which rotates around a spool axis, a housing for the spools, the take-up spool comprising a first face and the housing comprising a second face opposing the first face, and a rotational lock for the take-up spool configured to prevent inadvertent unwinding of test tape from at least the take-up spool, wherein the rotational lock comprises locking teeth disposed on each of the first and second faces, said teeth being shifted by an axial movement of the take-up spool along the spool axis between a mutually engaged position where the locking teeth of the take-up spool engage the locking teeth of the housing and a release position where the locking teeth of the take-up spool are axially spaced from the locking teeth of the housing.

2. The tape cassette according to claim 1, wherein the take-up spool is biased so that the locking teeth are in the engaged position.

3. The tape cassette according to claim 1, wherein the locking teeth can be moved from the mutually engaged position into the release position upon insertion of a drive spindle into the take-up spool.

4. The tape cassette according to claim 1, wherein the take-up spool can be rotated in both directions of rotation when the locking teeth are in the release position and wherein both directions of rotation of the take-up spool are locked when the locking teeth are in the engaged position.

5. The tape cassette according to claim 1, wherein the first face of the take-up spool comprises a disk, the locking teeth comprising teeth formed on the disk.

6. The tape cassette according to claim 5, wherein the take-up spool comprises a collar and a cylindrical spool body around which the used portions of the test tape can be wound, the collar comprising the disk, wherein the locking teeth on the disk face generally away from the cylindrical spool body.

7. The tape cassette according to claim 1, wherein the take-up spool is braced against the housing in the direction of the spool axis by a return spring.

8. The tape cassette according to claim 7, wherein the return spring comprises a leaf spring or spiral spring provided on a wall of the housing and wherein an annular space is kept generally vacant for receiving the unused portions of the test tape about the take-up spool between the wall and the locking teeth.

9. The tape cassette according to claim 1, wherein the second face of the housing comprises a ring flange, the locking teeth comprising teeth formed on said flange.

10. The tape cassette according to claim 1, wherein the locking teeth on the second face of the housing are formed on a portion of a ring segment facing away from a last deflecting point for the test tape to be wound on, and wherein a remaining portion of the ring segment has no teeth.

11. The tape cassette according to claim 1, wherein the locking teeth comprise teeth having asymmetric tooth flanks, wherein the tooth flanks which strike one another when the locking teeth are in the engaged position are steeper when rewinding the take-up spool.

12. The tape cassette according to claim 1, wherein the take-up spool is located in a chamber of the housing that is free of a physical axis of rotation.

13. The tape cassette according to claim 1, wherein the take-up spool can be placed on the locking teeth of the housing in any rotational position.

14. The tape cassette according to claim 1, wherein the take-up spool is float-mounted in the housing with transverse play relative to its spool axis.

15. The tape cassette according to claim 14, wherein the transverse play is between about 0.2 mm and about 0.6 mm.

16. The tape cassette according to claim 1, wherein the take-up spool has an annular extension which engages in an opening in the housing with transverse play at least in the engaged position of the locking teeth.

17. A diagnostic tape cassette for use with a blood glucose testing device, comprising: an analytical test tape, a supply spool and a take-up spool wherein unused portions of the analytical test tape are provided on the supply spool and unwound for use and wherein used portions of the analytical test tape are wound up onto the take-up spool that rotates around a spool axis, a housing for the spools and a rotational lock for the take-up spool, wherein the rotational lock comprises a locking spring attached to the housing and axially pretensioned against the take-up spool along the spool axis, and the locking spring includes at least one spring latch that meshes with free-wheel teeth arranged on the front of the take-up spool to prevent against unwinding of a tape loop.

18. The tape cassette according to claim 17, wherein the locking spring is formed on a wall of the housing as a concentric ring structure or spiral spring where an inner member of the locking spring projecting from the wall carries the at least one spring latch.

19. The tape cassette according to claim 17, wherein the at least one spring latch is designed as a multiple latch to subdivide the locked positions of the free-wheel teeth such that the individual latches are brought into a locking engagement which is displaced over the tooth pitch of the free-wheel teeth.

20. The tape cassette according to claim 17, wherein the free-wheel teeth are formed on an end wall of a spool body of the take-up spool which faces the locking spring, and wherein the spool body is supported on the housing by an annular collar and by locking teeth.

21. The tape cassette according to claim 17, wherein the free-wheel teeth are formed by a crown gear with an asymmetric tooth profile where the flatter tooth flanks form a slide slope for the at least one spring latch during rotation in the winding direction and the steeper tooth flanks block the at least one spring latch in a form-fitting manner during rotation in the unwinding direction.

22. The tape cassette according to claim 17, wherein the teeth of the free-wheel teeth have a tooth height which decreases over their width thus shortening the engagement length of the at least one spring latch.

* * * * *